United States Patent [19]

Umemoto et al.

[11] Patent Number: 5,374,732
[45] Date of Patent: Dec. 20, 1994

[54] CERTAIN SUBSTITUTED N-FLUOROPYRIDINIUMSULFONATES

[75] Inventors: Teruo Umemoto; Ginjiro Tomizawa, both of Tsykuba, Japan

[73] Assignee: Daikin Industries, Ltd., Osaka, Japan

[21] Appl. No.: 922,372

[22] Filed: Jul. 31, 1992

[30] Foreign Application Priority Data

Aug. 1, 1991 [JP] Japan ................ 3-192981
Feb. 21, 1992 [JP] Japan ................ 4-034854

[51] Int. Cl.$^5$ .................. C07D 213/71; C07D 213/20
[52] U.S. Cl. .................................... 546/294; 546/347; 546/348
[58] Field of Search ................ 546/294, 347, 348

[56] References Cited

U.S. PATENT DOCUMENTS

| | | | |
|---|---|---|---|
| 4,935,519 | 6/1990 | Van Der Puy et al. | 546/13 |
| 4,996,320 | 2/1991 | Umemoto et al. | 546/9 |
| 5,081,249 | 1/1992 | Umemoto | 546/294 |

FOREIGN PATENT DOCUMENTS

| | | | |
|---|---|---|---|
| 0182603 | 5/1986 | European Pat. Off. | 546/294 |
| 0204535 | 12/1986 | European Pat. Off. | 546/294 |
| 0393462 | 10/1990 | European Pat. Off. | 546/294 |

(List continued on next page.)

OTHER PUBLICATIONS

Differding et al., Helvetica Chimica Acta—vol. 72, pp. 1248-1249, (1989).
Banks et al., Journal of Fluorine Chemistry, vol. 46, pp. 297-305, (1990).
Satyamurthy et al., Journal of Organic Chemistry, vol. 55, pp. 3373-3374 (1990).
J. Chem. Soc. Perkin Trans. I 1988, pp. 2805-2811, "N-Halogeno Compounds Part 9.[1] N-Fluoroquinuclidinium Fluoride—A New . . . Agent.[2]".
Tetrahedron Letters, vol. 29, No. 47, pp. 4087-6090, 1988.
J. Chem. Soc., Chem. Commun., 1991, pp. 179-181.
Letters, Synlett, Mar. 1991, pp. 187-189, "N—Fluorobenzenesulfonimide: A Practical Reagent for Electrophilic Fluorinations".
Tetrahedron Letters, vol. 32, No. 13, pp. 1631-1634, 1991, Davis et al., "N-Fluoro-O-Benzenedisulfonimide . . .".
Journal of Fluorine Chemistry, 52 (1991) 389-401, Banks et al., "N-Halogeno Compounds . . .".
J. Am. Chem. Soc. 1991, 113, 2648-2651, Kol et al., "Isolation and Characterization of Methyl Hypofluorite (CH3OF)".
J. Org. Chem., 1983, 48 724-727, Lerman et la., "Acetyl (List continued on next page.)

*Primary Examiner*—Alan L. Rotman
*Attorney, Agent, or Firm*—Birch, Stewart, Kolasch & Birch

[57] ABSTRACT

A substituted N-fluoropyridiniumsulfonate of the formula:

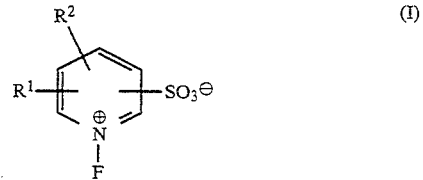

in which $R^1$ is a hydrogen atom, a halogen atom or a $C_1$-$C_4$ alkyl or haloalkyl group, and $R^2$ is a $C_1$-$C_4$ alkyl or haloalkyl group, which is an effective fluorinating agent.

6 Claims, No Drawings

FOREIGN PATENT DOCUMENTS 2-33707   7/1990   Japan .................................. 546/294
2-275859 11/1990  Japan .................................. 546/294
3-99062   4/1991   Japan .................................. 546/294

OTHER PUBLICATIONS

Hypofluroite, A New Moderating Carrier of Elemental Fluorine . . . Derivatives".

*J. Org. Chem.*, 1983, 48, 761–762, "1–Fluoro-2-pyridone: A Useful Fluroinating Reagent".

*Tetrahedron*, vol. 40, No. 1, pp. 189 to 197, 1984, Appelman et al., "The Reaction of Fluoroxysulfate . . . Acids".

*J. Am. Chem. Soc.*, 1984, 106, 452–454, Barnett.

*J. Org. Chem.*, 1986, 51, 222–225, Rozen et al., "A Novel Method for Constructing a CF2 Group via the Reaction of Alkynes . . . ".

*Tetrahedron Letters,* vol. 27, No. 37, pp. 4465–4468, 1986, Umemoto et al. "N–Fluoropyridinium Triflate and its Derivatives . . . ".

*J. Am. Chem. Soc.,* 1990, 112, 8563–8575, Umemoto et al., "Power and Structure–Variable Fluorinating Agents . . . ".

*Bull. Chem. Soc. Jpn.,* 64, 1981–1092 (1991) by Umemoto et al., "Synthesis and Properties of N–Fluropyridinium Salts".

CERTAIN SUBSTITUTED N-FLUOROPYRIDINIUMSULFONATES

BACKGROUND OF THE INVENTION

1. Field of the Invention

The present invention relates to a novel substituted N-fluoropyridiniumsulfonate having a lipophilic alkyl or haloalkyl group, intermediates for use in the preparation of said substituted N-fluoropyridiniumsulfonate and processes for preparing said substituted N-fluoropyridiniumsulfonate and said intermediates.

2. Description of the Related Art

For the fluorination of an organic compound, molecular fluorine ($F_2$) is known and used. Since a reaction between the molecular fluorine and the organic compound proceeds vigorously different from reactions with chlorine, bromine or iodine, its control is very difficult. Therefore, a development of a mild fluorinating agent which can be used in place of the molecular fluorine is one of important subjects in the industry.

As mild fluorinating agents which can be used in place of the molecular fluorine, following compounds have been developed:

acetyl hypofluorite (J. Org. Chem., 48, 724 (1983)); 1-fluoro-2-pyridone (J. Org. Chem., 48, 761 (1983)); cesium fluorooxysulfate (Tetrahedron, 40, 189 (1984)); N-fluoro-N-alkyltoluenesulfonamide (J. Am. Chem. Soc., 106, 452 (1984)); halogen monofluoride (J. Org. Chem., 51, 222 (1986)); N-fluoropyridinium salts (Tetrahedron Lett., 27, 4465 (1986), J. Am. Chem. Soc., 112, 8563 (1990), Bull. Chem. Soc. Jpn., 64, 1081 (1991), Japanese Patent Publication No. 33707/1990, Japanese Patent Kokai Publication Nos. 99062/1991 and 275859/1989, EP-A-393 462 and U.S. Pat. Nos. 4,996,320 and 4,935,519); N-fluoroquinuclidinium salts (J. Chem. Soc., Perkin Trans. I, 1988, 2805); N-fluorosaltum derivatives (Tetrahedron Lett., 29 6087 (1988)); N-fluoro-N,N-bis(trifluoromethanesulfonyl)amide (J. Chem. Soc., Chem. Commun., 1991, 179); N-fluoro-3,3-dimethyl-2,3-dihydro-1,2-benzenethiazole-1,1-dioxide (Helv. Chim. Act., 72, 1248 (1989)); N-fluoro-N-(pentafluoropyridyl)trifluoromethanesulfonamide (J. Fluorine Chem., 46, 297 (1990)); N-fluorolactam (J. Org. Chem., 55, 3373 (1990)); N-fluoro-N,N-bis(benzenesulfonyl)amide (Synlett, 1991, 187); N-fluoro-o-benzenedisulfonimide (Tetrahedron Lett., 32, 1631 (1991)); N-fluoroperfluoropiperidine (J. Fluorine Chem., 52, 389 (1991)); methyl hypofluorite (J. Am. Chem. Soc., 113, 2648 (1991)); and N-alkyl-N'-fluorotriethylenediammonium salts (J. Fluorine Chem., 54, 208 (1991)).

However, the above known fluorinating agents have some drawbacks in efficiency of fluorination, reaction selectivities, stability, handling properties, yields, reaction conditions, or regeneration efficiency of the fluorinating agents, and they do not satisfy the requirements of the industry. The regeneration of the fluorinating agent is a very important matter in view of economy and environmental pollution in the practical application of the fluorinating agent in the industry.

SUMMARY OF THE INVENTION

One object of the present invention is to provide a novel substituted N-fluoropyridinium salt which can be used as a fluorinating agent having good fluorination efficiency, reaction selectivity and easy regeneration.

Another object of the present invention is to provide an intermediate which is useful in the preparation of the novel substituted N-fluoropyridinium salt.

A further object of the present invention is to provide a process for preparing the novel substituted N-fluoropyridinium salt.

A yet further object of the present invention is to provide a process for preparing the above intermediate.

DETAILED DESCRIPTION OF THE INVENTION

According to a first aspect of the present invention, there is provided a substituted N-fluoropyridiniumsulfonate of the formula:

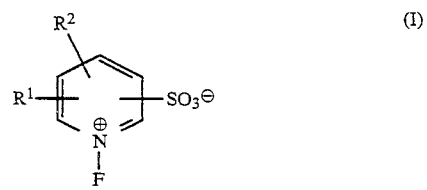

wherein $R^1$ is a hydrogen atom, a halogen atom or a $C_1$-$C_4$ alkyl or haloalkyl group, and $R^2$ is a $C_1$-$C_4$ alkyl or haloalkyl group.

Examples of the $C_1$-$C_4$ alkyl or haloalkyl group for $R^1$ and $R^2$ are straight or branched alkyl or haloalkyl groups such as $CH_3$—, $CH_3CH_2$—, $CH_3CH_2CH_2$—, $(CH_3)_2CH$—, $CH_3(CH_2)_2CH_2$—, $(CH_3)_2CHCH_2$—, $(CH_3)_3C$—, $CH_2F$—, $CHF_2$—, $CF_3$—, $CH_3CFH$—, $CH_2F$—$CH_2$—, $CH_3CF_2$—, $CHF_2CH_2$—, $CF_3CH_2$—, $CF_3CF_2$—, $CF_3CF_2CF_2$—, $(CF_3)_2CF$—, $CF_3(CF_2)_2CF_2$—, $(CF_3)_2CFCF_2$—, $CF_3CF_2(CF_3)CF$—, $CH_2Cl$—, $CHCl_2$—, $CCl_3$, $CFCl_2$—, $CF_2Cl$—, $CH_2ClCH_2$—, $CCl_3CH_2$—, $CCl_3CCl_2$—, $CH_2Br$—, $CHBr$—, $CBr_3$—, $CF_2Br$—, $CF_2HCF_2$—, $CF_2ICF_2$—, $CF_2BrCF_2$—, $CF_2ClCF_2$—, $CF_2HCF_2CF_2$—, $CF_2ClCF_2CF_2$—, $CF_2ICF_2CF_2$—, $(CF_3)_2CH$—, $(CF_3)_2CCl$—, $CF_2H(CF_2)_2CF_2$—, $CF_2Cl(CF_2)_2CF_2$—, $CF_2Br(CF_2)_2CF_2$—, $CF_2I(CF_2)_2CF_2$— and the like.

Specific examples of the substituted N-fluoropyridiniumsulfonate of the present invention are as follows:

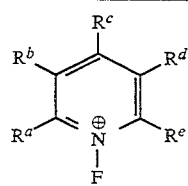

| $R^a$ | $R^b$ | $R^c$ | $R^d$ | $R^e$ |
|---|---|---|---|---|
| $CH_3$ | H | H | H | $SO_3^-$ |

-continued

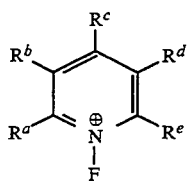

| $R^a$ | $R^b$ | $R^c$ | $R^d$ | $R^e$ |
|---|---|---|---|---|
| H | CH₃ | H | H | SO₃⁻ |
| H | H | CH₃ | H | SO₃⁻ |
| H | H | H | CH₃ | SO₃⁻ |
| CH₃ | H | H | SO₃⁻ | H |
| CH₃ | H | SO₃⁻ | H | H |
| CH₃ | SO₃⁻ | H | H | H |
| C₂H₅ | H | H | H | SO₃⁻ |
| C₂H₅ | H | H | SO₃⁻ | H |
| H | C₂H₅ | H | SO₃⁻ | H |
| H | H | C₂H₅ | H | SO₃⁻ |
| CH₂CH₂CH₃ | H | H | H | SO₃⁻ |
| CH₂CH₂CH₃ | H | H | SO₃⁻ | H |
| CH₂CH₂CH₃ | H | SO₃⁻ | H | H |
| CH(CH₃)₂ | H | H | H | SO₃⁻ |
| CH(CH₃)₂ | H | H | SO₃⁻ | H |
| H | CH₂CH₂CH₃ | H | SO₃⁻ | H |
| H | H | CH(CH₃)₂ | H | SO₃⁻ |
| H | H | H | CH₂CH₂CH₃ | SO₃⁻ |
| CH₂(CH₂)₂CH₃ | H | H | H | SO₃⁻ |
| CH₂CH(CH₃)₂ | H | H | H | SO₃⁻ |
| CH(CH₃)CH₂CH₃ | H | H | H | SO₃⁻ |
| C(CH₃)₃ | H | H | H | SO₃⁻ |
| H | CH₂(CH₂)₂CH₃ | H | H | SO₃⁻ |
| H | CH₂CH(CH₃)₂ | H | H | SO₃⁻ |
| H | CH(CH₃)CH₂CH₃ | H | H | SO₃⁻ |
| H | C(CH₃)₃ | H | H | SO₃⁻ |
| H | H | CH₂(CH₂)₂CH₃ | H | SO₃⁻ |
| H | H | CH₂CH(CH₃)₂ | H | SO₃⁻ |
| H | H | CH(CH₃)CH₂CH₃ | H | SO₃⁻ |
| H | H | C(CH₃)₃ | H | SO₃⁻ |
| H | H | H | CH₂(CH₂)₂CH₃ | SO₃⁻ |
| H | H | H | CH₂CH(CH₃)₂ | SO₃⁻ |
| CH₂(CH₂)₂CH₃ | H | SO₃⁻ | H | H |
| CH₂CH(CH₃)₂ | H | SO₃⁻ | H | H |
| C(CH₃)₃ | H | SO₃⁻ | H | H |
| CH₂(CH₂)₂CH₃ | H | H | SO₃⁻ | H |
| CH₂CH(CH₃)₂ | H | H | SO₃⁻ | H |
| CH₃ | H | H | SO₃⁻ | CH₃ |
| CH₃ | F | H | H | SO₃⁻ |
| CH₃ | Cl | H | H | SO₃⁻ |
| CH₃ | Br | H | H | SO₃⁻ |
| CH₃ | I | H | H | SO₃⁻ |
| CH₃ | H | Cl | H | SO₃⁻ |
| CH₃ | H | H | Cl | SO₃⁻ |
| CH₃ | H | H | F | SO₃⁻ |
| F | H | H | CH₃ | SO₃⁻ |
| F | H | SO₃⁻ | H | CH₃ |
| C₂H₅ | H | H | Cl | SO₃⁻ |
| CH₂CH₂CH₃ | H | H | Cl | SO₃⁻ |
| CH(CH₃)₂ | H | H | Cl | SO₃⁻ |
| CH₂(CH₂)₂CH₃ | H | SO₃⁻ | H | Cl |
| CH₂CH(CH₃)₂ | H | H | F | SO₃⁻ |
| CH(CH₃)CH₂CH₃ | Cl | H | SO₃⁻ | H |
| Cl | H | C(CH₃)₃ | H | SO₃⁻ |
| CH₃ | H | SO₃⁻ | H | CH₃ |
| CH₃ | H | CH₃ | H | SO₃⁻ |
| CH₃ | CH₃ | H | H | SO₃⁻ |
| H | CH₃ | H | CH₃ | SO₃⁻ |
| H | CH₃ | CH₃ | H | SO₃⁻ |
| CH₃ | SO₃⁻ | H | CH₃ | H |
| CH₃ | H | C₂H₅ | H | SO₃⁻ |
| CH₃ | H | CH₂CH₂CH₃ | H | SO₃⁻ |
| CH₃ | H | C(CH₃)₃ | H | SO₃⁻ |
| C₂H₅ | H | C₂H₅ | H | SO₃⁻ |
| C₂H₅ | H | H | SO₃⁻ | C₂H₅ |
| CH₂CH₂CH₃ | H | H | SO₃⁻ | CH₂CH₂CH₃ |
| CH(CH₃)₂ | H | CH(CH₃)₂ | H | SO₃⁻ |
| CH₂(CH₂)₂CH₃ | H | CH₂(CH₂)₂CH₃ | H | SO₃⁻ |
| CH₂(CH₂)₂CH₃ | H | H | SO₃⁻ | CH₂(CH₂)₂CH₃ |
| CH₂CH(CH₃)₂ | H | SO₃⁻ | H | CH₂CH(CH₃)₂ |
| CF₃ | H | H | H | SO₃⁻ |

-continued

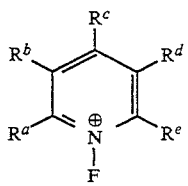

| $R^a$ | $R^b$ | $R^c$ | $R^d$ | $R^e$ |
|---|---|---|---|---|
| H | CF$_3$ | H | H | SO$_3^-$ |
| H | H | CF$_3$ | H | SO$_3^-$ |
| H | H | H | CF$_3$ | SO$_3^-$ |
| CCl$_3$ | H | H | H | SO$_3^-$ |
| H | CCl$_3$ | H | H | SO$_3^-$ |
| H | H | CCl$_3$ | H | SO$_3^-$ |
| H | H | H | CCl$_3$ | SO$_3^-$ |
| CFCl$_2$ | H | H | H | SO$_3^-$ |
| H | CFCl$_2$ | H | H | SO$_3^-$ |
| H | CF$_2$Cl | H | H | SO$_3^-$ |
| H | H | H | CF$_2$Cl | SO$_3^-$ |
| CBr$_3$ | H | H | H | SO$_3^-$ |
| H | H | CBr$_3$ | H | SO$_3^-$ |
| CBrCl$_2$ | H | H | H | SO$_3^-$ |
| H | CBr$_2$Cl | H | H | SO$_3^-$ |
| CFBr$_2$ | H | H | H | SO$_3^-$ |
| H | H | CF$_3$Br | H | SO$_3^-$ |
| CF$_3$ | H | H | SO$_3^-$ | H |
| CH$_2$F | H | CH$_3$ | H | SO$_3^-$ |
| CHF$_2$ | H | CH$_3$ | H | SO$_3^-$ |
| CF$_3$ | H | SO$_3^-$ | H | H |
| CF$_3$ | SO$_3^-$ | H | H | H |
| H | CF$_3$ | H | H | SO$_3^-$ |
| H | H | CF$_3$ | H | SO$_3^-$ |
| H | H | CF$_3$ | SO$_3^-$ | H |
| CCl$_3$ | H | H | SO$_3^-$ | H |
| CCl$_3$ | H | SO$_3^-$ | H | H |
| CCl$_3$ | SO$_3^-$ | H | H | H |
| CH$_2$F | H | H | H | SO$_3^-$ |
| H | CH$_2$F | H | H | SO$_3^-$ |
| H | H | CH$_2$F | H | SO$_3^-$ |
| H | H | H | CH$_2$F | SO$_3^-$ |
| CHF$_2$ | H | H | H | SO$_3^-$ |
| H | H | CHF$_2$ | H | SO$_3^-$ |
| H | CHF$_2$ | H | SO$_3^-$ | H |
| CH$_2$Cl | H | H | H | SO$_3^-$ |
| CH$_2$Br | H | H | H | SO$_3^-$ |
| CF$_3$ | F | H | H | SO$_3^-$ |
| CF$_3$ | Cl | H | H | SO$_3^-$ |
| H | CF$_3$ | H | F | SO$_3^-$ |
| H | C$_2$F$_5$ | H | Cl | SO$_3^-$ |
| H | CCl$_3$ | H | Cl | SO$_3^-$ |
| C$_2$F$_5$ | H | H | H | SO$_3^-$ |
| H | C$_2$F$_5$ | H | H | SO$_3^-$ |
| H | H | C$_2$F$_5$ | H | SO$_3^-$ |
| H | H | H | C$_2$F$_5$ | SO$_3^-$ |
| H | C$_2$F$_5$ | H | SO$_3^-$ | H |
| CF$_2$CF$_2$CF$_3$ | H | SO$_3^-$ | H | H |
| CF(CF$_3$)$_2$ | H | SO$_3^-$ | H | H |
| H | CF$_2$CF$_2$CF$_3$ | H | H | SO$_3^-$ |
| C(CF$_3$)$_3$ | H | H | H | SO$_3^-$ |
| H | CF(CF$_3$)CF$_2$CF$_3$ | H | SO$_3^-$ | H |
| H | H | CF$_2$CF(CF$_3$)$_2$ | H | SO$_3^-$ |
| CF$_2$(CF$_2$)$_2$CF$_3$ | SO$_3^-$ | H | H | H |
| C$_2$Cl$_5$ | H | H | H | SO$_3^-$ |
| H | H | C$_2$Cl$_5$ | H | SO$_3^-$ |
| CF$_2$HCF$_2$ | H | H | H | SO$_3^-$ |
| H | CF$_2$H(CF$_2$)$_2$ | H | H | SO$_3^-$ |
| H | H | CF$_2$H(CF$_2$)$_2$CF$_2$ | H | SO$_3^-$ |
| H | CFH$_2$CF$_2$ | H | H | SO$_3^-$ |
| H | H | (CF$_3$)$_2$CCl | H | SO$_3^-$ |
| CF$_3$ | CF$_3$ | H | H | SO$_3^-$ |
| CF$_3$ | H | CF$_3$ | H | SO$_3^-$ |
| CF$_3$ | H | H | CF$_3$ | SO$_3^-$ |
| H | CF$_3$ | CF$_3$ | H | SO$_3^-$ |
| H | CF$_3$ | H | CF$_3$ | SO$_3^-$ |
| CF$_3$ | CF$_3$ | H | SO$_3^-$ | CH$_2$ |
| CF$_3$ | H | SO$_3^-$ | H | CF$_3$ |
| CF$_3$ | SO$_3^-$ | H | H | CF$_3$ |
| CCl$_3$ | H | CCl$_3$ | H | SO$_3^-$ |
| CCl$_3$ | H | SO$_3^-$ | H | CCl$_3$ |

-continued

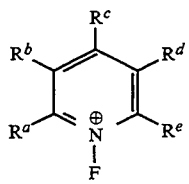

| $R^a$ | $R^b$ | $R^c$ | $R^d$ | $R^e$ |
|---|---|---|---|---|
| $CCl_3$ | H | H | $SO_3^-$ | $CCl_3$ |
| $CF_3$ | H | $CFCl_2$ | H | $SO_3^-$ |
| $CF_3$ | H | $CF_2Cl$ | H | $SO_3^-$ |
| $CF_3$ | H | $CH_3$ | H | $SO_3^-$ |
| $CH_3$ | H | $CF_3$ | H | $SO_3^-$ |
| $C_2F_5$ | H | $CF_3$ | H | $SO_3^-$ |
| $CF_2Cl$ | Cl | H | H | $SO_3^-$ |
| $CF_2CF_2Cl$ | H | H | Cl | $SO_3^-$ |
| $CF_2CF_2H$ | H | H | F | $SO_3^-$ |
| $CF_2(CF_2)_2CF_3$ | Cl | H | H | $SO_3^-$ |
| $C_2F_5$ | H | $C_2F_5$ | H | $SO_3^-$ |
| $C_2F_5$ | $C_2F_5$ | H | H | $SO_3^-$ |
| $CF(CF_3)_2$ | H | $CF(CF_3)_2$ | H | $SO_3^-$ |
| H | $CF_2CF_2CF_3$ | H | $CF_2CF_2CF_3$ | $SO_3^-$ |
| $CF_2(CF_2)_2CF_3$ | H | $CF_2(CF_2)_2CF_2$ | H | $SO_3^-$ |
| $CF_2(CF_2)_2CF_3$ | $CF_2(CF_2)_2CF_3$ | H | H | $SO_3^-$ |
| $CF_2(CF_2)_2CF_3$ | H | $SO_3^-$ | H | $CF_2(CF_2)_2CF_2$ |
| $CF_2(CF_2)_2CF_3$ | $SO_3^-$ | H | H | $CF_2(CF_2)_2CF_2$ |
| $CF_2(CF_2)_2CF_3$ | H | $CF_3$ | H | $SO_3^-$ |
| $C(CF_3)_3$ | H | $C_2F_5$ | H | $SO_3^-$ |
| $CF_2(CF_2)_2CF_3$ | H | $CF(CF_3)_2$ | H | $SO_3^-$ |
| $CF_2ClCF_2$ | H | H | H | $SO_3^-$ |
| $CF_2BrCF_2$ | H | $CF_2BrCF_2$ | H | $SO_3^-$ |
| $CF_2ICF_2$ | H | H | H | $SO_3^-$ |
| H | $CF_2BrCF_2CF_2$ | H | Cl | $SO_3^-$ |
| H | $CF_2I(CF_2)_2CF_2$ | H | H | $SO_3^-$ |
| $CF_2ClCF_2CF_2$ | H | $SO_3^-$ | H | $CF_2ClCF_2CF_2$ |

According to a second aspect of the present invention, there is provided a novel intermediate, a disubstituted pyridine-2-sulfonic acid or its salt of the formula:

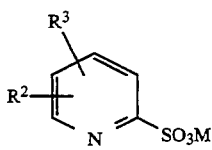

(II)

wherein $R^2$ is the same as defined above, $R^3$ is a halogen atom or a $C_1$–$C_4$ alkyl or haloalkyl group, and M is a hydrogen atom, a metal element or an ammonium group.

As the metal element, an alkali metal element and an alkaline earth element such as potassium, sodium, lithium, calcium, magnesium and the like are preferred. Examples of the ammonium group are $NH_4$, $NH(C_2H_5)_3$, $NH_2(C_2H_5)_2$, $NH_3(C_2H_5)$, $N(C_2H_5)_4$, $NH(CH_3)_3$, $NH_3(C_3H_7)$, $NH_3(C_4H_9)$, $N(C_4H_9)_4$ and the like.

Specific examples of the disubstituted pyridine-2-sulfonic acid or its salt are as follows:

| $R^a$ | $R^b$ | $R^c$ | $R^d$ | M |
|---|---|---|---|---|
| H | $CH_3$ | H | $CH_3$ | H |
| H | $CH_3$ | H | $CH_3$ | Na |
| H | $CF_3$ | H | $CF_3$ | H |
| H | $CH_3$ | H | $CH_3$ | $NH(C_2H_5)_3$ |
| H | $CH_3$ | H | $CH_3$ | K |
| H | $CH_3$ | H | $CH_3$ | Li |
| H | $CH_3$ | H | $CH_3$ | $NH(CH_3)_3$ |
| H | $CH_3$ | H | $CH_3$ | $NH_3C_2H_5$ |
| H | $CH_3$ | H | $CH_3$ | $MH_3C_3H_7$ |
| H | $CH_3$ | H | $CH_3$ | $NH_3C_4H_9$ |
| H | $CH_3$ | H | $CH_3$ | $NH_4$ |
| H | $CH_3$ | H | $CH_3$ | $N(C_2H_5)_4$ |
| H | $CF_3$ | H | $CF_3$ | K |
| H | $CF_3$ | H | $CF_3$ | Li |
| H | $CF_3$ | H | $CF_3$ | $NH_4$ |

-continued

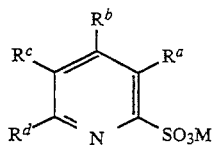

| $R^a$ | $R^b$ | $R^c$ | $R^d$ | M |
| --- | --- | --- | --- | --- |
| H | $CF_3$ | H | $CF_3$ | $NH(C_2H_5)_3$ |
| H | $CF_3$ | H | $CF_3$ | Na |
| $CF_3$ | H | $CF_3$ | H | H |
| $CF_3$ | H | H | $CF_3$ | H |
| H | H | $CF_3$ | $CF_3$ | H |
| H | H | $CF_3$ | $CF_3$ | ½ Mg |
| H | H | $CF_3$ | $CF_3$ | Cs |
| H | H | $CF_3$ | $CF_3$ | ½ Ca |
| $CH_3$ | H | $CH_3$ | H | H |
| H | $CH_3$ | $CH_3$ | H | H |
| H | $CH_3$ | H | $CH_2F$ | H |
| H | $CH_3$ | H | $CHF_2$ | H |
| H | $CH_3$ | H | $CF_3$ | H |
| H | $C_2H_5$ | H | $C_2H_5$ | H |
| H | $CH_2CH_2CH_3$ | H | $CH_2CH_2CH_3$ | H |
| H | $CH(CH_3)_3$ | H | $CH(CH_3)_3$ | H |
| H | $CH_2(CH_2)_2CH_3$ | H | $CH_2(CH_2)_2CH_3$ | H |
| H | $CH_2CH(CH_3)_2$ | H | $CH_2CH(CH_3)_2$ | H |
| H | $C(CH_3)_3$ | H | $C(CH_3)_3$ | H |
| $C_2H_5$ | H | $C_2H_5$ | H | H |
| H | $C(CH_3)_3$ | H | $CH_3$ | H |
| H | $C_2F_5$ | H | $C_2F_5$ | H |
| H | $CF_2CF_2CF_3$ | H | $CF_2CF_2CF_3$ | H |
| H | $CF(CF_3)_2$ | H | $CF(CF_3)_2$ | H |
| H | $CF_2(CF_2)_2CF_3$ | H | $CF_2(CF_2)_2CF_3$ | H |
| $CF_2Cl$ | H | H | $CF_3$ | H |
| $CF_3$ | H | H | $CF_2Cl$ | H |
| H | $CH_3$ | $CFCl_2$ | H | H |
| $CCl_3$ | H | H | $CH_3$ | H |
| H | $CCl_3$ | h | $CF_3CH_2$ | H |
| H | H | $CCl_3$ | $CF_3$ | H |
| H | $CF_3$ | H | $CCl_3$ | H |
| Br | H | H | $CBr_3$ | H |
| Br | H | $CBr_3$ | H | H |
| H | $CBr_3$ | H | Br | H |
| $CBr_3$ | H | $CBr_3$ | H | H |
| $CCl_3$ | H | H | $CCl_3$ | H |
| H | $CCl_3$ | H | $CCl_3$ | H |
| H | $CCl_3$ | $CCl_3$ | H | H |
| $CCl_3$ | $CCl_3$ | H | H | H |
| Cl | H | $CF_3$ | H | H |
| $CF_3$ | H | H | Cl | H |
| $CF_3$ | Cl | H | H | H |
| $CF_3$ | H | Cl | H | H |
| H | $CF_3$ | H | Cl | H |
| $CF_3$ | H | H | F | H |
| $CF_3$ | F | H | H | H |
| $CF_3$ | H | F | H | H |
| F | H | $CF_3$ | H | H |
| Br | H | $CF_3$ | H | H |
| I | H | $CF_3$ | H | H |
| $CCl_3$ | H | Cl | H | H |
| Cl | H | $CCl_3$ | H | H |
| Cl | $CCl_3$ | H | H | H |
| H | $CF_2H$ | H | $CF_2H$ | H |
| $CF_2CF_2CF_3$ | H | Cl | H | H |
| $CF_2CF_2Br$ | H | F | H | H |
| $CF_2CF_2CF_2I$ | H | H | I | H |
| H | Cl | H | $CFCl(CF_3)_2$ | H |

According to a third aspect of the present invention, there is provided a haloalkyl-substituted pyridine-2-sulfonic acid or its salt of the formula:

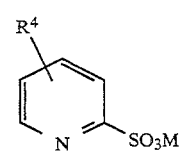

(III)

wherein M is the same as defined above, and $R^4$ is a $C_1$-$C_4$ haloalkyl group, and an alkyl-substituted pyridine-2-sulfonic acid or its salt of the formula:

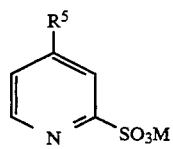

(IV)

wherein M is the same as defined above, and $R^5$ is an ethyl group or a tert.-butyl group.

wherein $R^1$ and $R^2$ are the same as defined above with molecular fluorine in the presence of an amine compound of the formula:

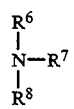

(VI)

wherein $R^6$, $R^7$ and $R^8$ are the same or different and each a hydrogen atom or a $C_1$-$C_8$ alkyl or aralkyl group.

Examples of the alkyl or aralkyl group for $R^6$ to $R^8$

| $R^a$ | $R^b$ | $R^c$ | $R^d$ | M |
|---|---|---|---|---|
| $CF_3$ | H | H | H | H |
| $CF_3$ | H | H | H | Li |
| $CF_3$ | H | H | H | Na |
| $CF_3$ | H | H | H | K |
| $CF_3$ | H | H | H | $NH_4$ |
| $CF_3$ | H | H | H | $NH(C_2H_5)_3$ |
| $CF_3$ | H | H | H | $NH_3CH_3$ |
| $CF_3$ | H | H | H | $N(C_2H_5)_4$ |
| $CF_3$ | H | H | H | $NH_3C_3H_7$ |
| $CF_3$ | H | H | H | $NH_3C_4H_9$ |
| H | $CF_3$ | H | H | $N(C_4H_9)_4$ |
| H | H | $CF_3$ | H | Cs |
| H | H | H | $CF_3$ | $\frac{1}{2}Mg$ |
| H | H | $C_2F_5$ | H | $\frac{1}{2}Ca$ |
| H | H | $CF_2CF_2CF_3$ | H | H |
| H | H | $CF(CF_3)_2$ | H | H |
| H | H | $CF_2(CF_2)_2CF_3$ | H | H |
| H | H | $CF_2CF(CF_3)_2$ | H | H |
| H | H | $CF(CF_3)CF_2CF_3$ | H | H |
| H | $CF_2(CF_2)_2CF_3$ | H | H | H |
| $CF(CF_3)_2$ | H | H | H | H |
| $CCl(CF_3)_2$ | H | H | H | H |
| $CF_2Cl$ | H | H | H | H |
| $CFCl_2$ | H | H | H | H |
| $CCl_3$ | H | H | H | H |
| H | $CCl_3$ | H | H | H |
| H | H | $CCl_3$ | H | H |
| H | H | H | $CCl_3$ | H |
| $CF_2ClCF_2$ | H | H | H | H |
| H | H | $CF_2ClCF_2$ | H | H |
| H | H | $CF_2BrCF_2$ | H | H |
| H | H | $CF_2ICF_2$ | H | H |
| H | H | H | $CF_2HCF_2$ | H |
| $C_2Cl_5$ | H | H | H | H |
| H | $CF_2CFHCF_3$ | H | H | H |
| H | H | $CF_2CFBrCF_3$ | H | H |
| H | H | H | $CF_2ICF_2CF_3$ | H |
| $CF_2I(CF_2)_2CF_2$ | H | H | H | H |
| H | H | $CF_2CI(CF_2)_2CF_2$ | H | H |
| H | H | H | $CF_2H(CF_2)_2CF_2$ | H |
| H | H | H | $CH_2F$ | H |
| H | H | H | $CH_2Cl$ | H |
| $CF_3CH_2$ | H | H | H | H |
| $CF_3CH_2CH_3$ | H | H | H | H |
| H | H | $CF_2HCF_2CH_2$ | H | H |
| H | H | H | $CF_2ICF_2CH_2CH_2$ | H |
| H | H | H | $CF_2H$ | H |
| H | H | H | $CCl_2H$ | H |
| $CH_3CF_2$ | H | H | H | H |

The substituted N-fluoropyridiniumsulfonate (I) of the present invention may be prepared by reacting a substituted pyridinesulfonic acid of the formula:

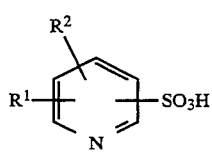

(V)

are $CH_3$—, $CH_3CH_2$—, $(CH_3)_2CH$—, $CH_3CH_2CH_2$—, $CH_3(CH_2)_2CH_2$—, $(CH_3)_3CHCH_2$—, $(CH_3)_3C$—, $CH_3(CH_2)_3CH_2$—, $CH_3CH_2C(CH_3)_2$—, $CH_3(CH_2)_4CH_2$—, $CH_3(CH_2)_5CH_2$—, $CH_3(CH_2)_6CH_2$—, $C_6H_5CH_2$—, $C_6H_5CH_2CH_2$—, $CH_3C_6H_4CH_2$— and the like.

Examples of the amine compound (VI) are ammonia, triethylamine, diethylamine, ethylamine, trimethylamine, dimethylamine, methylamine, propylamine, butylamine, pentylamine, hexylamine, heptylamine, octylamine, benzylamine, N,N-dimethylbenzylamine, xylylamine, phenethylamine, and the like.

An amount of the amine compound is from 0.8 to 1 mole per one mole of the substituted pyridinesulfonic acid.

Although the molecular fluorine may be used as such, it is preferably diluted with an inert gas to control the vigorous reaction so that an amount of the inert gas is from 99.9 to 50%. As the inert gas, nitrogen, helium or argon are preferably used.

The reaction is usually carried out by bubbling the diluted fluorine gas through a reaction mixture or jetting the diluted fluroine gas over a surface of the reaction mixture. Preferably, the reaction is carried out in a solvent. Preferred examples of the solvent are water, acetonitrile, propionitrile, acetone, chloroform, methylene chloride, carbon tetrachloride and the like.

A reaction temperature is usually from $-80°$ C. to $+40°$ C., preferably from $-60°$ C. to $+25°$ C.

The above process is a new process and in the scope of the present invention.

In addition to the above new process, the substituted N-fluoropyridiniumsulfonate (I) can be prepared by oxidizing a mercaptopyridine derivative of the formula:

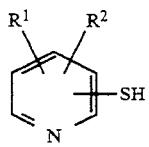

(VII)

wherein $R^1$ and $R^2$ are the same as defined above or a dipyridyldisulfide derivative of the formula:

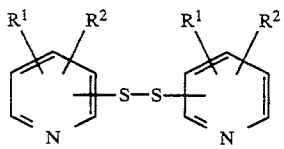

(VIII)

wherein $R^1$ and $R^2$ are the same as defined above, optionally neutralizing a product with a base to obtain a substituted pyridinesulfonic acid or its salt of the formula:

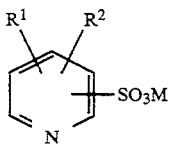

(IX)

wherein $R^1$, $R^2$ and M are the same as defined above, and then fluorinating the substituted pyridinesulfonic acid or its salt.

The mercaptopyridine derivative or the dipyridyldisulfide is oxidized with an oxidizing agent such as hydrogen peroxide, nitric acid, potassium permanganate, peracid, and the like. Among them, nitric acid is preferred. An amount of the oxidizing agent is at least 3 moles per one mole of the mercaptopyridine derivative or a half mole of the pyridyldisulfide derivative. To prepare the disubstituted pyridinesulfonic acid at a high yield, the oxidizing agent is preferably used in an excess amount.

In the oxidation reaction, the oxidizing agent may act as a reaction medium. When the oxidizing agent is a solid compound or when the reaction is intended to proceed mildly or at a good yield, a solvent is used. Examples of the solvent are water, acetonitrile, acetic acid, trifluoroacetic acid, acetone, chloroform, methylene chloride, carbon tetrachloride, and the like. A reaction temperature is usually from $0°$ to $200°$ C., preferably from $20°$ to $170°$ C.

Examples of the base used for neutralization are alkali metal hydroxide (e.g. sodium hydroxide, potassium hydroxide, lithium hydroxide, etc.), alkali metal hydrides (e.g. sodium hydride, potassium hydride, lithium hydride, etc.), alkali metals (e.g. sodium, potassium, lithium, etc.) ammonia, amines (e.g. methylamine, dimethylamine, trimethylamine, ethylamine, diethylamine, triethylamine, propylamine, butylamine, etc.), ammonium hydroxides (e.g. tetramethylammonium hydroxide, tetraethylammonium hydroxide, etc.) and the like.

An amount of the base is an equimolar amount to the substituted pyridinesulfonic acid (corresponding to the formula (IX) wherein M is a hydrogen atom). For neutralization, a solvent is not necessarily used. For smooth neutralization, a solvent is preferably used. Examples of the solvent are water, methanol, ethanol, propanol, butanol, acetonitrile, tetrahydrofuran, ether, dioxane and the like.

The mercaptopyridine derivative and the dipyridyldisulfide derivative are commercially available or prepared by a per se conventional methods.

The fluorination may be carried out by the above described conventional method.

A substituted pyridine-2-sulfonic acid of the formula:

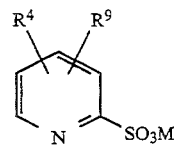

(X)

wherein $R^4$ is a $C_1$-$C_4$ haloalkyl group and $R^9$ is a hydrogen atom, a halogen atom or a $C_1$-$C_4$ haloalkyl group, or its salt can be prepared by reacting a substituted 2-halopyridine of the formula:

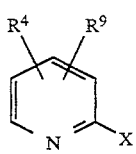

(XI)

wherein $R^4$ and $R^9$ are the same as above, and X is a halogen atom, with a sulfite salt and optionally treating a produced compound with an acid.

Examples of the sulfite salt are $NaHSO_3$, $Na_2SO_3$, $KHSO_3$, $K_2SO_3$, $LiHSO_3$, $Li_2SO_3$, $RbHSO_3$, $CsHSO_3$, $Cs_2SO_3$, $MgSO_3$, $CaSO_3$, $BaSO_3$, $(NH_4)HSO_3$, $(NH_4)_2SO_3$, $(CH_3NH_3)HSO_3$, $(CH_3NH_3)_2SO_3$, $[(CH_3)_2NH_2]HSO_3$, $[(CH_3)_2NH_2]HSO_3$, $[(CH_3)_3NH]HSO_3$, $[(CH_3)_3NH]_2SO_3$, $(CH_3)_4NHSO_3$, $[(CH_3)_4N]_2SO_3$, $(C_2H_5NH_3)HSO_3$, $(C_2H_5NH_3)_2SO_3$, $[(C_2H_5)_2NH_2]HSO_3$, $[(C_2H_5)_3NH]_2SO_3$, $(C_2H_5)_4NH$ $SO_3$, $[(C_2H_5)_4N]_2SO_3$, $(C_3H_7NH_3)_2SO_3$, $(C_4H_9NH_3)_2SO_3$, $(C_4H_9 NH_3)HSO_3$, $[(C_4H_9)_4N]_2SO_3$, (PhCH$_2$NH$_3$)HSO$_3$, (PhCH$_2$NH$_3$)$_2$SO$_3$, [PhCH$_2$N(CH$_3$)$_3$]HSO$_3$, [PhCH$_2$N(CH$_3$)$_3$]$_2$SO$_3$, and their hydrates.

Examples of the reaction solvent are water, methanol, ethanol, propanol, isopropanol, butanol, isobutanol, tert.-butanol, ethylene glycol, diethylene glycol and mixtures thereof.

As the acid, any one of conventionally used ones may be used. Preferred examples are sulfuric acid, halosulfuric acid, hydrochloric acid, hydrobromic acid, hydroiodic acid, hydrogen chloride, hydrogen bromide, hydrogen iodide, phosphoric acid, acetic acid, trihaloacetic acid (e.g trifluoroacetic acid), cation exchange resins, and the like.

A temperature in the above reaction is usually from 0° to 200° C., preferably from 20° to 150° C.

The compound of the present invention can be used as a fluorinating agent for fluorinating any of organic or inorganic compounds, preferably organic compounds, in particular, nucleophilic organic compounds.

PREFERRED EMBODIMENTS OF THE INVENTION

The present invention will be illustrated by following Examples.

Example 1

Preparation of
N-Fluoro-4-methylpyridinum-2-sulfonate

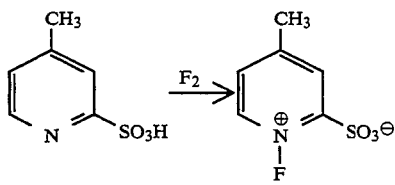

In a reactor, 4-methylpyridine-2-sulfonic acid (3.46 g, 20 mmol) was dissolved in a mixture of acetonitrile (60 ml) and water (6 ml). The reactor was dipped in a cooling bath kept at −20° C., and fluorine gas diluted with nitrogen gas to a concentration of 10% was introduced at a flow rate of 40 ml/min. A total amount of the fluorine gas was 1334 ml (60 mmol). Then, the nitrogen gas alone was introduced at a flow rate of 36 ml/min. for 30 minutes. After the addition of tetrahydrofuran and ethyl ether at −20° C., a crystalline precipitate was recovered by filtration at room temperature. The crystal was washed with ethyl ether and dried under reduced pressure to obtain crystalline N-fluoro-4-methylpyridinium-2-sulfonate (3.04 g, 15.9 mmol). Yield, 80%. A melting point is shown in Table 1. IR and NMR data are as follows:

IR (Nujol): 3160, 3080, 1598, 1285, 1275, 1250, 1100, 1040, 885, 800, 700, 630 cm$^{-1}$.

$^1$H-NMR (in CD$_3$CN): δ(ppm)=2.66 (3H, s, CH$_3$), 7.85 (1H, m, H$_5$), 8.41 (1H, dd, $J_{H3-F}$=5.7 Hz, $J_{H3-5}$=2.8 Hz, H$_3$), 8.84 (1H, dd, $J_{H6-F}$=14.2 Hz, $J_{H6-5}$=7.1 Hz, H$_6$).

$^{19}$F-NMR (in CD$_3$CN; external standard: CF$_3$COOH): −109.5 ppm.

Elemental analysis (C$_6$H$_6$FNO$_3$S): Calc.: C, 37.70; H, 3.16; N, 7.33 Found: C, 37.87; H, 2.92; N, 7.40

Examples 2–4

In the same manner as in Example 1 except using a raw material and a solvent in Table 1, a reaction was carried out.

The NMR data and the result of elemental analysis of the products are as follows:

Example 2

$^1$H-NMR (in CD$_3$CN): δ(ppm)=8.42 (1H, ddd, $J_{H4-5}$=7.8 Hz, $J_{H4-F}$=0.67 Hz, H$_4$), 8.28 (1H, ddd, $J_{H3-4}$=7.8 Hz, $J_{H3-4}$=5.8 Hz, $J_{H3-5}$=2.0 Hz, H$_3$), 7.94 (1H, ddd, $J_{H5-4}$=7.8 Hz, $J_{H5-F}$=7.8 Hz, $J_{H5-3}$=2.1 Hz, H$_5$), 2.86 (3H, d, $J_{H-F}$=4.2 Hz, CH$_3$).

$^{19}$F-NMR (in CD$_3$CN; internal standard: CFCl$_3$): −27.72 ppm.

Elemental analysis (C$_6$H$_6$FNO$_3$S): Calc.: C, 37.70; H, 3.16; N, 7.33 Found: C, 37.87; H, 2.95; N, 7.39

Example 3

$^1$H-NMR (in CD$_3$CN): δ (ppm)=1.32 (3H, t, J=7.6 Hz, —CH$_2$CH$_3$), 3.0 (2H, q, J=7.6 Hz, —CH$_2$CH$_3$), 7.91 (1H, m, H$_5$), 8.30 (1H, dd, $J_{H3-5}$=2.8 Hz, $J_{H3-F}$=5.7 Hz, H$_3$), 8.91 (1H, dd, $J_{H6-F}$=14.2 Hz, $J_{H6-5}$=7.1 Hz, H$_6$).

$^{19}$F-NMR (in CD$_3$CN; external standard: CF$_3$COOH): −110.0 ppm.

Elemental analysis (C$_7$H$_8$FNO$_3$S): Calc.: C, 40.97; H, 3.93; N, 6.83 Found: C, 41.10; H, 3.84; N, 6.90

Example 4

$^1$H-NMR (in CD$_3$CN): δ (ppm)=1.41 (9H, s, 3×CH$_3$; tert.-Bu), 8.07 (1H, ddd, $J_{H5-6}$=7.09 Hz, $J_{H5-F}$=3.88 Hz, $J_{H5-3}$=3.02 Hz, H$_5$), 8.38 (1H, dd, $J_{H3-F}$=6.01 Hz, $J_{H3-5}$=3.18 Hz, H$_3$), 8.93 (1H, dd, $J_{H6-F}$=14.17 Hzm $J_{H6-5}$=7.37 Hz, H$_6$).

$^{19}$F-NMR (in CD$_3$CN; external standard: CFCl$_3$): 31.7 ppm.

Elemental analysis (C$_9$H$_{12}$FNO$_3$S): Calc.: C, 46.34; H, 5.19; N, 6.00 Found: C, 46.12; H, 5.43; N, 6.22

TABLE 1

| Ex. No. | Raw material | Solvent | Product | Yield | M.P. (°C.) |
|---|---|---|---|---|---|
| 1 | 4-methylpyridine-2-sulfonic acid | CH$_3$CN—H$_2$O (10:1) | N-fluoro-4-methylpyridinium-2-sulfonate | 80% | 203–208 |

TABLE 1-continued

| Ex. No. | Raw material | Solvent | Product | Yield | M.P. (°C.) |
|---|---|---|---|---|---|
| 2 | (4-methylpyridine-2-sulfonic acid) | CH$_3$CN—H$_2$O (10:1) | (N-fluoro-4-methylpyridinium-2-sulfonate) | 65% | 192–195 |
| 3 | (4-ethylpyridine-2-sulfonic acid) | CH$_3$CN | (N-fluoro-4-ethylpyridinium-2-sulfonate) | 79% | 196.5–198.5 (Decomp.) |
| 4 | (4-tert-butylpyridine-2-sulfonic acid) | CH$_3$CN—H$_2$O (20:1) | (N-fluoro-4-tert-butylpyridinium-2-sulfonate) | 84% | 237–240 |

Example 5

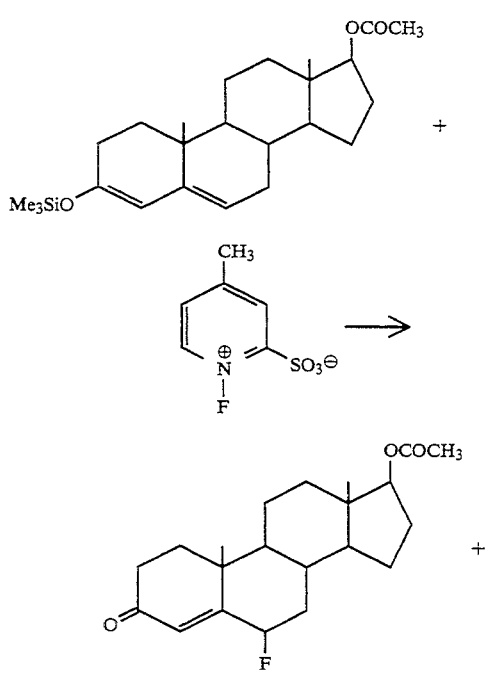

+

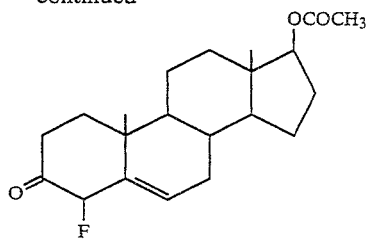

In an argon atmosphere, 17β-acetoxy-3-trimethylsilyloxy-3,5-androstadiene (402 mg, 1 mmol), N-fluoro-4-methylpyridinium-2-sulfonate (191 mg, 1 mmol) and anhydrous methylene chloride (4 ml) were stirred at room temperature for 30 hours. After adding water to the reaction mixture, it was extracted with methylene chloride. The organic layer was dried over magnesium sulfate and concentrated. Analysis of the residue by $^{19}$F-NMR revealed that 17β-acetoxy-6-fluoro-3,5-androstene and 17β-acetoxy-4-fluoro-3,5-androstene were produced at yields of 68% and 4%, respectively, which mean that a molar ratio of the 6-fluoroisomer to the 4-fluoroisomer was 17:1. As to the configuration of the fluorine atom at the 6-position of the 6-fluoroisomer, a ratio of α/β was 1/3.9.

Examples 6–9 and Comparative Examples 1–4

In the same manner as in Example 5 but using a raw material and a fluorinating agent shown in Tables 2 and 3 and changing the reaction time as shown in Tables 2 and 3, the reaction was carried out. The results are shown in Tables 2 and 3.

TABLE 2

Steroid with OR" at 17-position and R'O at 3-position (diene) → Fluorinating agent in $CH_2Cl_2$, R.T. → 6-F product + 4-F product

| Ex. No. | Raw material | Fluorinating agent | Time (hrs) | Product (%) 6-F | Product (%) 4-F |
|---|---|---|---|---|---|
| 5 | R' = SiMe₃<br>R" = COCH₃ | 4-CH₃ substituted N-F pyridinium sulfonate | 30 | 68% | 4% |
| 6 | R' = SiMe₃<br>R" = COCH₃ | 4-CH₂CH₃ substituted N-F pyridinium sulfonate | 24 | 67% | 5% |
| 7 | R' = SiMe₃<br>R" = COCH₃ | 4-C(CH₃)₃ substituted N-F pyridinium sulfonate | 24 | 70% | 7% |
| 8 | R' = SiEt₃<br>R" = COCH₃ | 4-CH₃ substituted N-F pyridinium sulfonate | 48 | 92% | 1% |
| 9 | R' = Si(i-Pr)₃<br>R" = COCH₃ | 4-CH₃ substituted N-F pyridinium sulfonate | 90 | 93% | 0% |

TABLE 3

Reaction scheme: 17β-OR″, 3-OR′ androstadiene + Fluorinating agent in CH₂Cl₂, R.T. → 6-F isomer + 4-F isomer

| C. Ex. No. | Raw material | Fluorinating agent | Time (hrs) | Product (%) 6-F | 4-F |
|---|---|---|---|---|---|
| 1 | R′ = SiMe₃<br>R″ = COCH₃ | N-fluoropyridinium triflate | 4 | 36% | 15% |
| 2 | R′ = Si(i-Pr)₃<br>R″ = COCH₃ | N-fluoropyridinium triflate | 2.5 | 33% | 8% |
| 3 | R′ = SiMe₃<br>R″ = COCH₃ | N-fluoropyridinium sulfonate | 47 | 24% | 2% |
| 4 | R′ = SiMe₃<br>R″ = SiMe₃ | N-fluoro-2-chloro-6-sulfonatopyridinium | 2.5 | 0% | 0% |

As shown in Tables 2 and 3, when the conventional fluorinating agents were used for the fluorination of 17β-acetoxy-3-trimethylsilyloxy-3,5-antrostadiene (Comparative Examples 1-4), the desired useful 6-fluoroisomer was not generated or even if generated the yield was very low, while the 4-fluoroisomer was generated in a considerably high ratio. When the novel N-fluoropyridiniumsulfonate of the present invention was used (Examples 5-9) as the fluorinating agent, the yield and the ratio of the 6-fluoroisomer to the 4-fluoroisomer were very high.

Example 10

Preparation of 4-tert.-butyl-2-pyridinesulfonic acid

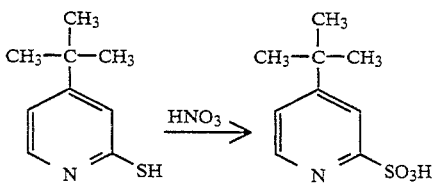

To 4-tert.-butyl-2-pyridinethiol (16.7 g, 0.1 mol) in a reactor, a mixture of water (225 ml) and conc. 65% nitric acid (75 ml) was poured and heated on a bath kept at about 90° C. till the generation of gas ceased. After the reaction, the produced floating material was filtered off through a glass filter, and a filtrate was concentrated. To the residue, ethanol was added and the mixture was kept standing. The generated crystal was recovered by filtration to obtain crystalline 4-tert.-butyl-2-pyridinesulfonic acid (18.9 g, 87.7 mmol). Yield, 88%. Melting point, 296°–297° C.

IR (KBr): 1618, 1465, 1440, 1265, 1240, 1200, 1160, 1100, 860, 770, 735, 690, 625 cm$^{-1}$.

$^1$H-NMR (in D$_2$O; internal standard: Me$_3$SiCD$_2$CD$_2$COONa): δ (ppm)=1.4 (9H, s, 3CH$_3$), 7.97 (1H, dd, J$_{H5-6}$=5.7 Hz, J$_{H5-3}$=2.0 Hz, H$_5$), 8.22 (1H, d, J$_{H3-5}$=2.0 Hz, H$_3$), 8.62 (1H, d, J$_{H6-5}$=5.7 Hz, H$_6$).

Example 11

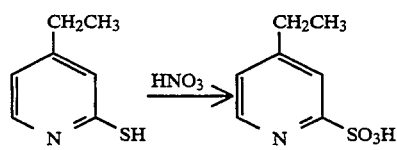

In the same manner as in Example 10 except that 4-ethyl-2-pyridinethiol was used in place of 4-tert.-butyl-2-pyridinethiol, the reaction was carried out to obtain 4-ethyl-2-pyridinesulfonic acid. Yield, 65%. Melting point, 221°–223° C.

IR (KBr): 1620, 1575, 1480, 1380, 1310, 1180, 1120, 1090, 980, 805 cm$^{-1}$.

$^1$H-NMR (in D$_2$O; internal standard: Me$_3$SiCD$_2$CD$_2$COONa): δ (ppm)=1.34 (3H, t, J=7.1 Hz, —CH$_2$CH$_3$), 2.02 (2H, q, J=7.1 Hz, —CH$_2$CH$_3$), 7.95 (1H, dm, J$_{H5-6}$=5.7 Hz, H$_5$), 8.19 (1H, bs, H$_3$), 8.63 (1H, d, J$_{H6-5}$=5.7 Hz, H$_6$).

Example 12

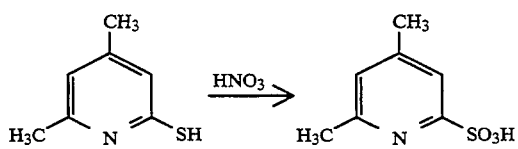

In a 2 liter beaker, 70% nitric acid (150 ml) and water (450 ml) were charged and heated at 75° C. To the heated mixture, 4,6-dimethyl-2-mercaptopyridine (27.8 g, 0.2 mol) was gradually added and reacted at 90° C. for 30 minutes. The reaction mixture was filtered through a glass filter and the filtrate was concentrated. To the residue, ethanol was added. A precipitated crystal was recovered by filtration, washed with ethanol, ethyl acetate and ether successively and dried to obtain 4,6-dimethylpyridine-2-sulfonic acid (26 g). Yield, 70%. Decomposition point, 316°–330° C.

Elemental analysis: Calc.: C, 44.91; H, 4.85; N, 7.48 Found: C, 44.93; H, 4.73; N, 7.48

IR (KBr): 3447, 3240, 3070, 2928, 1630, 1609, 1508, 1457, 1395, 1376, 1262, 1228, 1151, 1054, 947, 868, 722, 641 cm$^{-1}$.

MS (SIMS method): Calc.: 188.03814 (C$_7$H$_{10}$NO$_3$S) Found: 188.03850

$^1$H-NMR (in D$_2$O; internal standard: Me$_3$SiCD$_2$CD$_2$COONa): δ (ppm)=2.63 (3H, s, 4-CH$_3$), 2.76 (3H, s, 6-CH$_3$), 7.75 (1H, bs, 5-H), 7.98 (1H, bs, 3-H).

Example 13

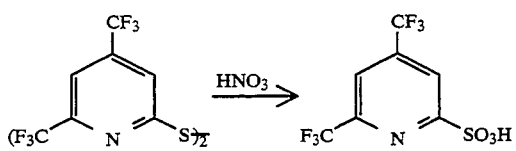

In a 300 ml flask, bis[2-[4,6-di(trifluoromethyl)-pyridyl]]disulfide (10 g) and 70% nitric acid (100 ml) were charged and reacted on an oil bath kept at 150° C. for 5 hours. After concentrating the reaction mixture, water was added to the residue, and the mixture was extracted with ethyl ether. The aqueous layer was concentrated and dried under reduced pressure to obtain 4,6-(bistrifluoromethyl)pyridine-2-sulfonic acid (4.91 g). Yield, 41%. Melting point, 193°–195° C.

Elemental analysis (C$_7$H$_3$F$_6$NO$_3$S.1.5H$_2$O): Calc.: C, 26.10; H, 1.88; N, 4.35 Found: C, 25.72; H, 1.30; N, 4.22

IR (Nujol): 2360, 1282, 1237, 1143, 1046, 686 cm$^{-1}$.

MS (SIMS method): Calc.: 295.98161 (C$_7$H$_4$F$_6$NO$_3$S) Found: 295.98260

$^1$H-NMR (in CD$_3$CN; internal standard: TMS): δ (ppm)=8.27 (1H, bs), 8.41 (1H, bs).

$^{19}$F-NMR (in CD$_3$CN: δ (ppm)=−63.9 (3F, s), −67.2 (3F, s).

Example 14

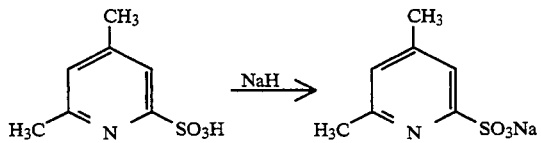

In a 50 ml flask, sodium hydride (60% in oil) (200 mg, 5 mmol) and tetrahydrofuran (10 ml) were charged, and then 4,6-dimethylpyridine-2-sulfonic acid (935 mg) was gradually added at room temperature. Then, the mixture was stirred at room temperature for about 30 minutes. After the addition of a small amount of ethanol to the reaction mixture, the precipitated crystal was recovered by filtration. The crystal was washed with ethyl acetate and diethyl ether successively and dried to obtain sodium 4,6-dimethyl-2-pyridinesulfonate (1.05 g) at a quantitative yield. Melting point, 257°–258° C.

Elemental analysis: Calc.: C, 40.19; H, 3.85; N, 6.70 Found: C, 40.04; H, 3,75; N, 6.62

IR (KBr): 3406, 1607, 1227, 1053, 870, 654 cm$^{-1}$.

$^1$H-NMR (in D$_2$O; internal standard: Me$_3$SiCD$_2$CD$_2$COONa): δ (ppm)=2.40 (3H, s, 4-CH$_3$), 2.52 (3H, s, 6-CH$_3$), 7.29 (1H, bs, 5-H), 7.60 (1H, bs, 3-H).

Example 15

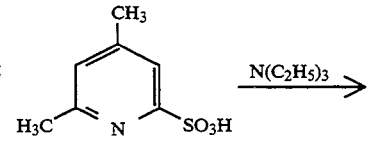

-continued

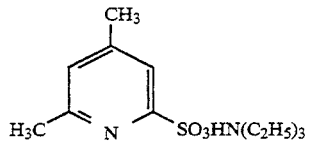

In an egg-plant type flask, 4,6-dimethylpyridine-2-sulfonic acid (374 mg, 2 mmol) and acetonitrile (4 ml) were charged, and then triethylamine (0.31 ml, 2.2 mmol) was added and stirred at room temperature for 1 hour. The reaction mixture was concentrated and dried under reduced pressure to obtain 4,6-dimethylpyridine-2-sulfonic acid triethylamine at a quantitative yield. Decomposition point, 270°–290° C.

$^1$H-NMR (in CDCl$_3$): δ (ppm)=1.40 (9H, t, J=7.3 Hz, CH$_2$CH$_3$), 2.33 (3H, s, 4-CH$_3$), 2.51 (3H, s, 6-CH$_3$), 3.24 (6H, q, J=7.3 Hz CH$_2$CH$_3$), CH$_2$CH$_3$), 6.97 (1H, m, 5-H), 7.71 (1H, m, 3-H).

Example 16

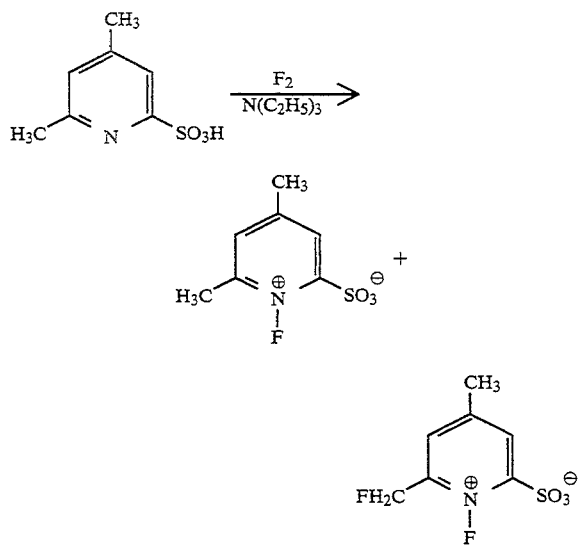

To a mixture of acetonitrile (4 ml) and water (0.4 ml), 4,6-dimethylpyridine-2-sulfonic acid (374 mg, 2 mmol) and triethylamine (202 mg, 2 mmol) were added. To the stirred mixture cooled on a bath kept at −40° C., a fluorine gas diluted with nitrogen gas to a concentration of 10% was introduced. The total amount of the fluorine gas was 140 ml. As the fluorination reaction proceeded, a precipitate was formed. After the reaction, only the nitrogen gas was introduced for 30 minutes. After the addition of ethyl ether to the mixture, the resulting precipitate was recovered by filtration to obtain a crystalline material (356 mg). The analysis of the crystalline material by $^1$H-NMR and $^{19}$F-NMR revealed that it was a mixture of N-fluoro-4,6-dimethylpyridinium-2-sulfonate and N-fluoro-6-fluoromethyl-4-methylpyridinium-2-sulfonate in a molar ratio of 10:1. The yields of the former and the latter were 78% and 8%, respectively. Recrystallization gave a pure compound of the former.

N-Fluoro-4,6-dimethylpyridinium-2-sulfonate
Melting point: 207°–212° C. (with decomposition)
Elemental analysis: Calc.: C, 40.97; H, 3.93; N, 6.83
Found: C, 40.69; H, 3.84; N, 6.90

IR (Nujol): 3080, 1608, 1467, 1263, 1141, 1054, 855, 763, 634 cm$^{-1}$.
MS (SIMS method): Calc.: 206.02872 (C$_7$H$_9$FNO$_3$S) Found: 206.02890

$^1$H-NMR (in CD$_3$CN): δ (ppm)=2.60 (3H, m, 4-CH$_3$), 2.79 (3H, d, J$_{H-F}$=4.1 Hz, 6-CH$_3$), 7.75 (1H, dd, J$_{H-F}$=6.2 Hz, J$_{H3-5}$=2.7 Hz, 5-H), 8.12 (1H, dd, J$_{H-F}$=5.4 Hz, J$_{H3-5}$=2.7 Hz, 3-H).

$^{19}$F-NMR (in CD$_3$CN; internal standard: CFCl$_3$): δ (ppm)=19.8 (bs, N-F).

N-Fluoro-6-fluoromethyl-4-methylpyridinium-2-sulfonate $^1$H-NMR (in CD$_3$CN): δ (ppm)=8.27 (1H, dd, J$_{H-F}$=5 Hz, J$_{H3-5}$=2.5 Hz, 3-H), 7.97 (1H, dd, J$_{H-F}$=5 Hz, J$_{H3-5}$=2.5 Hz, 5-H), 5.89 (2H, dm, J$_{H-F}$=44.5 Hz, CH$_2$F), 2.70 (3H, m, CH$_3$).

$^{19}$F-NMR (in CD$_3$CN; internal standard: CFCl$_3$): δ (ppm)=18.2 (1F, bs, N-F), −229.4 (1F, td, J$_{H-F}$=44.5 Hz, J$_{F-F}$=4.0 Hz, CH$_2$F).

Example 17

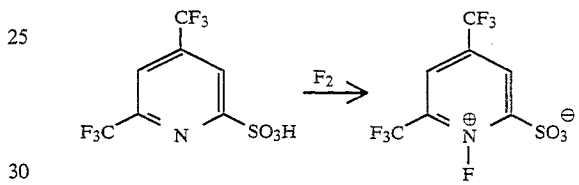

In a 25 ml flask, acetonitrile (6 ml) was added to 4,6-bistrifluoromethylpyridine-2-sulfonic acid (874 mg, 2.64 mmol) to prepare a homogeneous mixture. Then, the flask was dipped in a cooling bath kept at −40° C., and to the mixture, the fluorine gas diluted with the nitrogen gas to a concentration of 10% was introduced at a flow rate of 15 ml/min. The total amount of the fluorine gas was 211 ml. As the fluorination reaction proceeded, a precipitate was formed. After the reaction, only the nitrogen gas was introduced for 30 minutes. After the addition of ethyl ether to the mixture, the resulting precipitate was recovered by filtration to obtain N-fluoro-4,6-bistrifluoromethylpyridinium-2-sulfonate (787 mg). Yield, 95%. Melting point, 172°–174° C. (with decomposition).

Elemental analysis: Calc.: C, 26.85; H, 0.64; N, 4.47
Found: C, 26.60; H, 0.85; N, 4.43
IR (Nujol): 3105, 3074, 1348, 1281, 1194, 1158, 1113, 1091, 1060, 950, 916, 818, 668, 612 cm$^{-1}$.
MS (FAB method): Calc.: 313.97219 (C$_7$H$_3$F$_7$NO$_3$S) Found: 313.97250

$^1$H-NMR (in a mixture of CF$_3$COOD and CD$_3$CN (2:1)): δ (ppm)=8.97 (1H, dd, J$_{H-F}$=4.7 Hz, J$_{H3-5}$=2.5 Hz), 9.26 (1H, dd, J$_{H-F}$=4.6 Hz, J$_{H3-5}$=2.5 Hz).

$^{19}$F-NMR (in CD$_3$CN; internal standard: CFCl$_3$): δ (ppm)=35.5 (1F, d, J$_{F-F}$=21 Hz, N-F), −62.2 (3F, d, J$_{F-F}$=21 Hz, 6-CF$_3$), −63.7 (3F, s, 4-CF$_3$).

Example 18

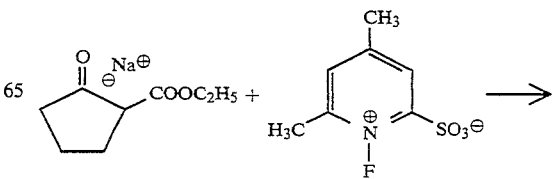

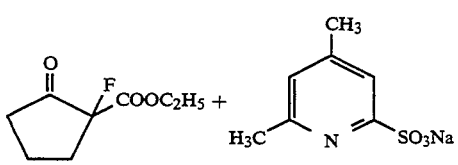

In an inert gas atmosphere, to a mixture of sodium hydride (120 mg, 3 mmol) and tetrahydrofuran (6 ml), ethyl 2-oxocyclopentanecarboxylate (445 μl, 3 mmol) was added and then N-fluoro-4,6-dimethylpyridinium-2-sulfonate (615 mg) was added while cooling with ice, followed by stirring at room temperature for 1.5 hours. The reaction mixture was filtrated and the obtained crystal was washed with tetrahydrofuran and ethyl ether successively to obtain sodium 4,6-dimethylpyridine-2-sulfonate (535 mg). Yield, 85%.

The filtrate was concentrated. To the residue, water was added, and the mixture was extracted with ethyl ether. The ether layer was dried over anhydrous sodium sulfate. After filtration, the filtrate was concentrated and the residue was subjected to the silica gel column chromatography and eluted with a mixed solvent of methylene chloride and n-hexane (1:1) to obtain ethyl 1-fluoro-2-oxocyclopentanecarboxylate at a yield of 72%. The NMR date of this product was identical with that of the standard sample.

Example 19

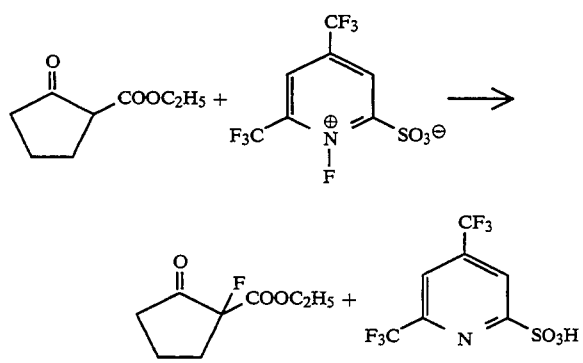

In an inert gas atmosphere, to a mixture of tetrahydrofuran (2 ml), N-fluoro-4,6-bistrifluoromethylpyridinium-2-sulfonate (273 mg, 0.872 mmol) and ethyl 2-oxocyclopentanecarboxylate (129 μl, 0.872 mmol) were added and reacted at room temperature for 46 hours. After adding water, the reaction mixture was extracted with ethyl ether. The ether layer was dried over anhydrous magnesium sulfate and concentrated. To the residue, fluorobenzene was added, and the mixture was quantitatively analyzed by $^{19}$F-NMR to find that ethyl 1-fluoro-2-oxocyclopentanecarboxylate was produced at a yield of 84%.

Example 20

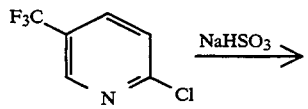

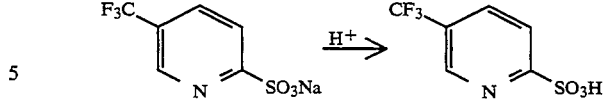

In a flask, 2-chloro-5-(trifluoromethyl)pyridine (54.5 g, 0.3 mol), sodium hydrogen sulfite (125 g, 1.2 mol), ethanol (600 ml) and water (600 ml) were charged and heated under reflux for 198 hours. After evaporating off the solvent, to the solid residue, conc. hydrochloric acid was added. The mixture was evaporated to dryness. The residue was extracted with methanol and filtrated. The filtrate was evaporated to dryness to obtain sodium 5-(trifluoromethyl)pyridine-2-sulfonate (64.0 g). Yield, 86%. Decomposition point, 356°-370° C.

Elemental analysis ($C_6H_3F_3NNaO_3S \cdot 1/2H_2O$): Calc.: C, 27.92; H, 1.56; N, 5.43 Found: C, 27.86; H, 1.46; N, 5.37

IR (KBr): 3526, 1579, 1576, 1387, 1333, 1256, 1220, 1168, 1132, 1076, 1050, 1022, 854, 726, 655 cm$^{-1}$.

MS (FAB method): 250 (M$^+$+1)

$^1$H-NMR (in D$_2$O; internal standard: Me$_3$SiCD$_2$CD$_2$COONa): δ (ppm)=8.12 (1H, dm, J=8.3 Hz, 3-H), 8.39 (1H, dm, J=8.3 Hz, 4-H), 8.97 (1H, m, 6-H).

$^{19}$F-NMR (in dimethylsulfoxide; internal standard: CFCl$_3$): δ (ppm)=−60.3 (s, CF$_3$).

When sodium 5-(trifluoromethyl)pyridine-2-sulfonate was treated with a cation exchange resin, it was quantitatively converted to 5-(trifluoromethyl)pyridine-2-sulfonic acid having the melting point of 290°-315° C. (with decomposition).

Elemental analysis: Calc.: C, 31.72; H, 1.77; N, 6.17 Found: C, 31.71; H, 1.68; N, 6.13

IR (KBr): 3430, 3100, 3039, 2618, 2087, 1618, 1431, 1379, 1327, 1291, 1229, 1188, 1151, 1080, 1051, 1028, 930, 865, 799, 718, 632 cm$^{-1}$.

MS (FAB method): 228 (M$^+$+1).

$^1$H-NMR (in D$_2$O): δ (ppm)=8.11 (1H, dm, J=8.3 Hz, 3-H), 8.38 (1H, dm, J=8.3 Hz, 4-H), 8.96 (1H, m, 6-H).

$^{19}$F-NMR (in dimethylsulfoxide; internal standard: CFCl$_3$): δ (ppm)=−60.4 (s, CF$_3$).

Example 21

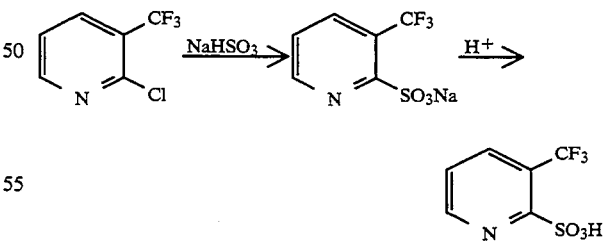

In a flask, 2-chloro-3-(trifluoromethyl)pyridine (20.0 g, 110 mmol), sodium hydrogen sulfite (46 g, 442 mmol), ethanol (200 ml) and water (200 ml) were charged and heated under reflux for 138 hours. After evaporating off the solvent from the reaction mixture, conc. hydrochloric acid was added to the residue and then evaporated to dryness. This residue was extracted with methanol, and the methanol phase was filtered and evaporated to dryness to obtain sodium 3-(trifluoromethyl)pyridine-2-sulfonate (18.6 g). Yield, 68%.

$^1$H-NMR (in D$_2$O; internal standard: Me$_3$SiCD$_2$CD$_2$COONa): δ (ppm)=7.80 (1H, ddm, J=7.6 and 4.8 Hz, 5-H), 8.41 (1H, dm, J=7.6 Hz, 4-H), 8.78 (1H, dm, J=4.8 Hz, 6-H).

$^{19}$F-NMR (in dimethylsulfoxide; internal standard: CFCl$_3$): δ (ppm)=−56.7 (s, CF$_3$).

Sodium 3-(trifluoromethyl)pyridine-2-sulfonate was treated with a cation exchange resin to obtain 3-(trifluoromethyl)pyridine-2-sulfonate quantitatively. Melting point, 280°–310° C. (with decomposition).

Elemental analysis: Calc.: C, 31.72; H, 1.77; N, 6.17 Found: C, 31.78; H, 1.77; N, 6.10

IR (KBr): 3434, 3162, 3104, 1622, 1523, 1448, 1318, 1297, 1237, 1169, 1145, 1065, 1036, 992, 929, 814, 722, 651, 618 cm$^{-1}$.

MS (FAB method): 228 (M$^+$+1).

$^1$H-NMR (in D$_2$O; internal standard: Me$_3$SiCD$_2$CD$_2$COONa): δ (ppm)=7.82 (1H, ddm, J=8.1 and 4.9 Hz, 5-H, 8.44 (1H, dm, J=8.1 Hz, 4-H), 8.79 (1H, dm, J=4.9 Hz, 6-H).

$^{19}$F-NMR (in dimethylsulfoxide; internal standard: CFCl$_3$): δ (ppm)=−56.5 (s, CF$_3$).

Example 22

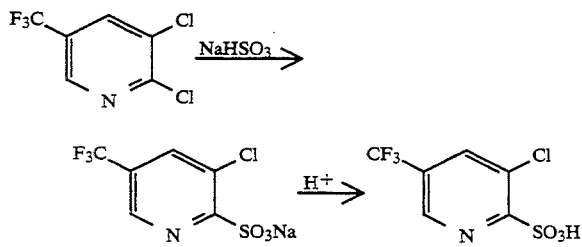

In a flask, 2,3-dichloro-5-(trifluoromethyl)pyridine (10.8 g, 50 mmol), sodium hydrogen sulfite (20.8 g, 200 mmol), ethanol (100 ml) and water (100 ml) were charged and heated under reflux for 41 hours. After evaporating off the solvent from the reaction mixture, conc. hydrochloric acid was added to the residue and then evaporated to dryness. This residue was extracted with methanol, and the metanol phase was filtered and evaporated to dryness to obtain quantitatively sodium 5-trifluoromethyl-3-chloropyridine-2-sulfonate (14.6 g). Decomposition point, 322°–334° C.

IR (KBr): 3578, 3510, 1626, 1599, 1378, 1324, 1248, 1170, 1138, 1092, 1075, 1042, 924, 862, 732, 686, 650 cm$^{-1}$.

MS (FAB method): 285 (M$^+$), 283 (M$^+$)

$^1$H-NMR (in D$_2$O; internal standard: Me$_3$SiCD$_2$CD$_2$COONa): δ (ppm)=8.49 (1H, m, 4-H), 8.85 (1H, m, 6-H).

$^{19}$F-NMR (in dimethylsulfoxide; internal standard: CFCl$_3$): δ (ppm)=−60.3 (s, CF$_3$).

Sodium 5-trifluoromethyl-3-chloropyridine-2-sulfonate was treated with a cation exchange resin to obtain 5-trifluoromethyl-3-chloropyridine-2-sulfonic acid quantitatively. Melting point, 310°–325° C. (with decomposition).

Elemental analysis: Calc.: C, 27.55; H, 1.16; N, 5.35 Found: C, 27.42; H, 1.08; N, 5.27

IR (KBr): 3110, 2954, 2922, 2853, 1621, 1521, 1461, 1399, 1357, 1320, 1285, 1234, 1187, 1146, 1112, 1072, 1038, 880, 862, 736, 680, 636 cm$^{-1}$.

MS (Negative FAB method): 262 (M$^+$−1), 260 (M$^+$1).

$^1$H-NMR (in D$_2$O; internal standard: Me$_3$SiCD$_2$CD$_2$COONa): δ (ppm)=8.47 (1H, m, 4-H), 8.83 (1H, m, 6-H).

$^{19}$F-NMR (in dimethylsulfoxide; internal standard: CFCl$_3$): δ (ppm)=−60.3 (s, CF$_3$).

Example 23

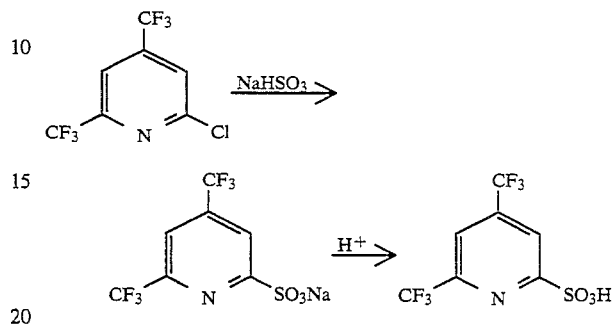

A mixture of 2-chloro-4,6-bis(trifluoromethyl)pyridine (2.50 g, 10 mmol), sodium hydrogen sulfite (4.2 g, 40 mmol), ethanol (40 ml) and water (40 ml) was heated under reflux for 96.5 hours. The reaction mixture was evaporated to dryness under reduced pressure. To the residue, conc. hydrochloric acid was added and the mixture was again evaporated to dryness. The residued was extracted with methanol, and a methanol phase was filtered. The filtrate was evaporated to dryness under reduced pressure to obtain sodium 4,6-bis(trifluoromethyl)pyridine-2-sulfonate (2.11 g). Yield, 66%.

The resulting sodium salt was dissolved in a small amount of conc. hydrochloric acid and extracted with ethyl ether. From the ether phase, ethyl ether was evaporated off to obtain 4,6-bis(trifluoromethyl)pyridine-2-sulfonic acid in a convertion of 64%, which was identical with that obtained in Example 13.

Example 24

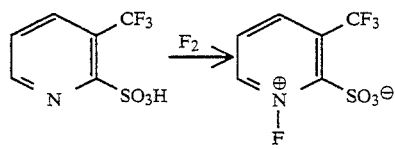

To a mixture of 3-(trifluoromethyl)pyridine-2-sulfonic acid (115 mg, 0.5 mmol) and acetonitrile (20 ml) in a flask on a cooling bath kept at −10° C., a mixed gas of 10% fluorine/90% nitrogen was introduced at a flow rate of 15 ml/min. The total amount of the fluorine gas was 1.5 mmol. Thereafter, the nitrogen gas alone was introduced for 30 minutes. After the reaction mixture was concentrated, ethyl acetate was added to the residue. The precipitated crystal was recovered by filtration to obtain N-fluoro-3-(trifluoromethyl)pyridinium-2-sulfonate (84.6 mg, 0.345 mmol). Yield, 69%. Melting point, 180°–196° C. (with decomposition).

Elemental analysis: Calc.: C, 29.40; H, 1.23; N, 5.71 Found: C, 29.42; H, 1.24; N, 5.67

IR (Nujol): 3440, 3161, 3094, 2957, 2851, 2340, 2008, 1660, 1582, 1466, 1423, 1319, 1276, 1227, 1184, 1132, 1074, 1056, 900, 806, 768, 708, 626 cm$^{-1}$.

MS (FAB method): 246 (M$^+$+1).

$^1$H-NMR (in CD$_2$CN): δ (ppm)=8.25 (1H, m, 5-H), 8.94 (1H, ddm, J=8.4 and 1.2 Hz, 4-H), 9.26 (1H, ddd, J=14.5, 7.0 and 1.2 Hz, 6-H).

$^{19}$F-NMR (in CD$_3$CN; internal standard: CFCl$_3$): δ (ppm)=48.4 (1F, m, N-F), −56.1 (3F, s, CF$_3$).

Example 25

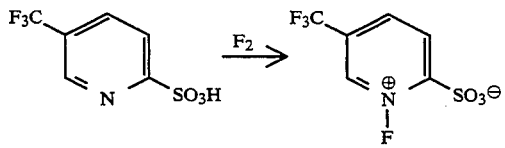

To a mixture of 5-(trifluoromethyl)pyridine-2-sulfonic acid (227 mg, 1 mmol) and acetonitrile (60 ml) in a flask on a cooling bath kept at −10° C., a mixed gas of 10% fluorine/90% nitrogen was introduced at a flow rate of 15 ml/min. The total amount of the fluorine gas was 3.1 mmol. Thereafter, the nitrogen gas alone was introduced for 30 minutes. After the reaction mixture was concentrated, ethyl acetate was added to the residue. The precipitated crystal was recovered by filtration to obtain N-fluoro-5-(trifluoromethyl)pyridinium-2-sulfonate (212 mg, 0.86 mmol). Yield, 86%. Melting point, 190°–220° C. (with decomposition).

Elemental analysis: Calc.: C, 29.40; H, 1.23; N, 5.71 Found: C, 29.21; H, 1.09; N, 5.85

IR (KBr): 3058, 2924, 2853, 1662, 1622, 1577, 1398, 1337, 1262, 1204, 1153, 1074, 1044, 909, 876, 700 cm$^{-1}$.

MS (FAB method): Calc.: 245.98480 (C$_6$H$_4$NF$_4$O$_3$S) Found: 245.98589

$^1$H-NMR (in CD$_2$CN): δ (ppm)=9.66 (1H, dd, J=13.5 and 0.9 Hz, 6-H), 8.90 (1H, dm, J=8.2 Hz, 4-H), 8.69 (1H, ddm, J=8.2 and 6.2 Hz, 3-H).

$^{19}$F-NMR (in CD$_3$CN; internal standard: CFCl$_3$): δ (ppm)=44.5 (1F, bs, N-F), −61.9 (3F, s, CF$_3$).

Example 26

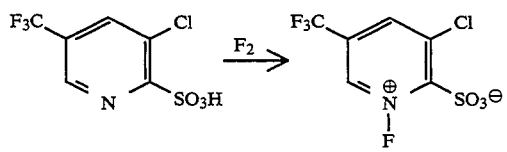

To a mixture of 3-chloro-5-(trifluoromethyl)pyridine-2-sulfonic acid (262 mg, 1 mmol) and acetonitrile (60 ml) in a flask on a cooling bath kept at −10° C., a mixed gas of 10% fluorine/90% nitrogen was introduced at a flow rate of 15 ml/min. The total amount of the fluorine gas was 3.6 mmol. Thereafter, the nitrogen gas alone was introduced for 30 minutes. After the reaction mixture was concentrated, ethyl acetate was added to the residue. The precipitated crystal was recovered by filtration to obtain N-fluoro-3-chloro-5-(trifluoromethyl)-pyridinium-2-sulfonate (231 mg, 0.83 mmol). Yield, 83%. Melting point, 220°–250° C. (with decomposition).

Elemental analysis: Calc.: C, 25.77; H, 0.72; N, 5.01 Found: C, 25.49; H, 0.79; N, 4.87

IR (Nujol): 3057, 1386, 1325, 1296, 1276, 1210, 1161, 1073, 1056, 940, 873, 722, 636 cm$^{-1}$.

MS: 278, 276, 262, 260, 198, 196.

$^1$H-NMR (in CD$_3$CN): δ (ppm)=9.03 (1H, m, 4-H), 9.26 (1H, dm, J=13.4 Hz, 6-H).

$^{19}$F-NMR (in CD$_3$CN; internal standard: CFCl$_3$): δ (ppm)=53.5 (1F, m, N-F), −61.8 (3F, s, CF$_3$).

Example 27

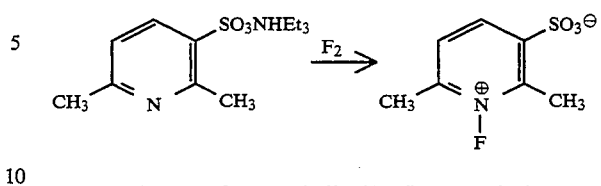

To a mixture of acetonitrile (4 ml) and 2,6-dimethyl-pyridine-3-sulfonic acid (410 mg, 2 mmol), triethylamine (404 mg, 4 mmol) was added at room temperature while stirring, followed by evaporation to dryness under reduced pressure to obtain 2,6-dimethylpyridine-3-sulfonic acid triethylamine salt. The triethylamine salt was dissolved in acetonitrile (4 ml). To the resulting solution cooled with a cooling bath kept at −20° C., a mixed gas of 10% fluorine/ 90% nitrogen was introduced at a flow rate of 15 ml/min. The total amount of the fluorine gas was 6 mmol. Thereafter, the nitrogen gas alone was introduced for 30 minutes. Ethyl acetate was added to the reaction mixture. The precipitated crystal was recovered by filtration to obtain N-fluoro-2,6-dimethylpyridinium-3-sulfonate (257 mg). Yield, 63%. Decomposition point, 200°–210° C.

Elemental analysis: Calc.: C, 40.97; H, 3.93; N, 6.83 Found: C, 40.75; H, 3.75; N, 6.64

IR (Nujol): 3090, 3021, 1607, 1581, 1487, 1467, 1441, 1232, 1185, 1144, 1057, 1024, 698, 666 cm$^{-1}$.

MS (FAB method): 206 (M$^+$+1).

$^1$H-NMR (in D$_2$O; internal standard: Me$_3$SiCD$_2$CD$_2$COONa): δ (ppm)=2.93 (3H, 4, J=4.5 Hz, CH$_3$), 3.13 (3H, d, J=4.7 Hz, CH$_3$), 8.06 (1H, ddm, J=8.4 and 7.5 Hz, 5-H), 8.83 (1H, d, J=8.4 Hz, 4-H).

$^{19}$F-NMR (in dimethylsulfoxide; internal standard: CFCl$_3$): δ (ppm)=25.9 (1F, bs, N-F).

Example 28

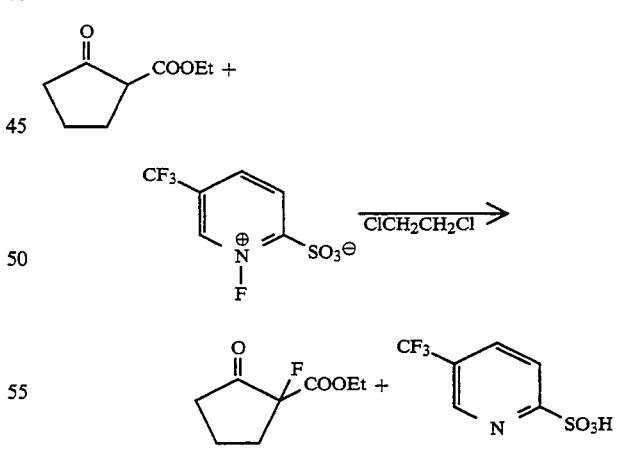

A mixture of ethyl 2-oxocyclopentanecarboxylate (148 μl, 1 mmol), N-fluoro-5-(trifluoromethyl)pyridinium-2-sulfonate (245 mg, 1 mmol) and 1,2-dichloroethane (2 ml) was heated under reflux in an argon atmosphere for 6 hours. Thereafter, the precipitate was recovered by filtration and washed with methylene chloride to obtain 5-trifluoromethylpyridine-2-sulfonic acid (217 mg). Yield, 96%. Analysis of the filtrate by $^{19}$F-NMR revealed that ethyl 1-fluoro-2-oxocyclopentanecarboxylate was produced at a yield of 57%.

Example 29

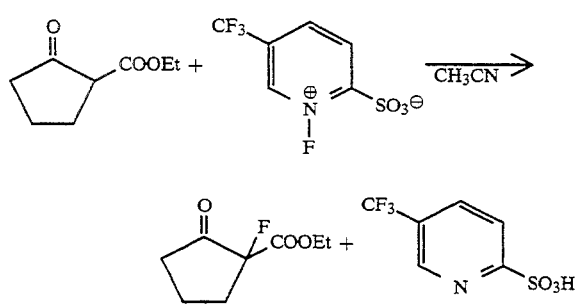

A mixture of ethyl 2-oxocyclopentanecarboxylate (148 μl, 1 mmol), N-fluoro-5-(trifluoromethyl)pyridinium-2-sulfonate (245 mg, 1 mmol) and acetonitrile (2 ml) was heated under reflux in an argon atmosphere for 5 hours. From the reaction mixture, the solvent was evaporated off under reduced pressure. To the residue, methylene chloride was added to recover undissolved 5-trifluoromethylpyridine-2-sulfonic acid. After drying, its weight was 194 mg. Yield 86%. Analysis of the filtrate by ¹⁹F-NMR revealed that ethyl 1-fluoro-2-oxocyclopentanecarboxylate was produced at a yield of 62%.

Example 30

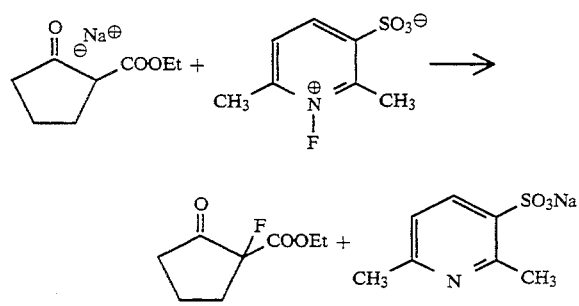

In a solution of ethyl 2-oxocyclopentanecarboxylate (148 μl, 1 mmol) in dimethylsulfoxide (2 ml), sodium hydride (60% in an oil) (40 mg, 1 mmol) was added while stirring at room temperature, followed by stirring for 10 minutes to obtain a sodium salt of ethyl 2-oxocyclopentanecarboxylate. To this sodium salt, N-fluoro-2,6-dimethylpyridinium-3-sulfonate (205 mg, 1 mmol) was added and stirred for 10 minutes. To the reaction mixture, water was added. Then, the mixture was extracted with ethyl ether. The ethyl ether layer was dried over anhydrous sodium sulfate and filtered. The filtrate was concentrated and analyzed by ¹⁹F-NMR to find that ethyl 1-fluoro-2-oxocyclopentanecarboxylate was obtained at a yield of 39%.

Example 31

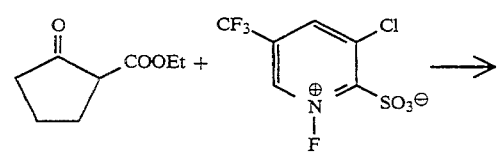

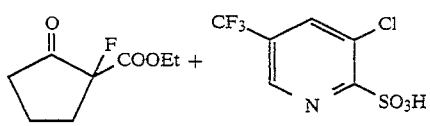

A mixture of ethyl 2-oxocyclopentanecarboxylate (148 μl, 1 mmol), N-fluoro-3-chloro-5-(trifluoromethyl)pyridinium-2-sulfonate (280 mg, 1 mmol) and acetonitrile (2 ml) was heated under reflux in an argon atmosphere for 30 minutes. From the reaction mixture, the solvent was evaporated off under reduced pressure. To the residue, methylene chloride was added to recover undissolved 3-chloro-5-(trifluoromethyl)pyridine-2-sulfonic acid. After drying, its weight was 217 mg. Yield 83%. Analysis of the filtrate by ¹⁹F-NMR revealed that ethyl 1-fluoro-2-oxocyclopentanecarboxylate was produced at a yield of 75%.

Examples 32–34 and Comparative Example 5

Using a fluorinating agent shown in Table 4, phenol was fluorinated in trichloroethane at 100° C. The reaction times and yields are shown in Table 4.

As seen from the results in Table 4, the fluorinating agent of Comparative Example 5 took 2 to 1000 times longer time than the fluorinating agents of the present invention to achieve substantially the same yield.

TABLE 4

| | Fluorinating agent | Time | Yield |
|---|---|---|---|
| Ex. 32 | 4-CH₃ pyridinium-2-SO₃⁻, N-F | 24 hr | 57% |
| Ex. 33 | 5-F₃C pyridinium-2-SO₃⁻, N-F | 18 hr | 59% |
| Ex. 34 | 4-CF₃, 6-CF₃ pyridinium-2-SO₃⁻, N-F | 0.05 hr | 69% |
| C. E. 5 | 6-Cl pyridinium-2-SO₃⁻, N-F | 49 hr | 56% |

The substituted N-fluoropyridiniumsulfonate of the present invention is excellent in the fluorination efficiency and reaction selectivity, can be easily prepared and is stable in an air so that its handling property is very good. When it is used for fluorination, the raw material substituted pyridinesulfonic acid or its salt is easily recovered. This means that the substituted N-fluoropyridiniumsulfonate is easily regenerated.

What is claimed is:

1. A substituted N-fluoropyridiniumsulfonate of the formula

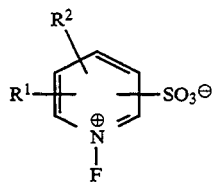

(I)

wherein $R^1$ is a hydrogen atom, a halogen atom or a $C_1$–$C_4$ alkyl or $C_1$–$C_4$ haloalkyl group, and $R^2$ is a $C_1$–$C_4$ alkyl or $C_1$–$C_4$ haloalkyl group.

2. A substituted N-fluoropyridiniumsulfonate compound having the formula

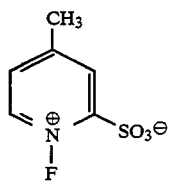

3. A substituted N-fluoropyridiniumsulfonate compound having the formula

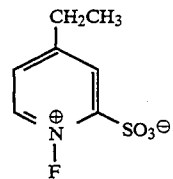

4. A substituted N-fluoropyridiniumsulfonate compound having the formula

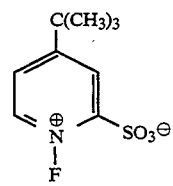

5. A substituted N-fluoropyridiniumsulfonate compound having the formula

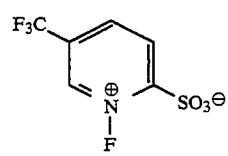

6. A substituted N-fluoropyridiniumsulfonate compound having the formula

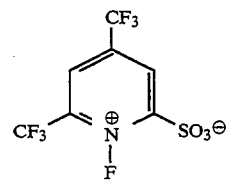

* * * * *

UNITED STATES PATENT AND TRADEMARK OFFICE
CERTIFICATE OF CORRECTION

PATENT NO. : 5,374,732
DATED : Dec. 20, 1994
INVENTOR(S) : Teruo Umemoto, et al

It is certified that error appears in the above-indentified patent and that said Letters Patent is hereby corrected as shown below:

ON THE COVER:

Item [75], line 2, change "Tsykuba" to --Tsukuba--.

Signed and Sealed this

Sixth Day of June, 1995

Attest:

BRUCE LEHMAN

Attesting Officer

Commissioner of Patents and Trademarks